US00PP37661P2

(12) United States Plant Patent
Lin et al.

(10) Patent No.: US PP37,661 P2
(45) Date of Patent: Sep. 1, 2026

(54) ***ANTHURIUM* PLANT NAMED 'KARINA'**

(50) Latin Name: *Anthurium andraeanum*
Varietal Denomination: KARINA

(71) Applicant: Zhongshan Brighten Floriculture Co., Ltd, Zhongshan City (CN)

(72) Inventors: Fazhuang Lin, Sanming (CN); Fengqin Yao, Sanming (CN)

(73) Assignee: Zhongshan Brighten Floriculture Ltd (CN)

( * ) Notice: Subject to any disclaimer, the term of this patent is extended or adjusted under 35 U.S.C. 154(b) by 0 days.

(21) Appl. No.: 19/406,904

(22) Filed: Dec. 2, 2025

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365
See application file for complete search history.

(56) References Cited

U.S. PATENT DOCUMENTS

PP28,458 P2 * 9/2017 Van Dijk ..... A01H 6/00 Plt./384

* cited by examiner

*Primary Examiner* — Susan Mccormick Ewoldt
*Assistant Examiner* — Zachariah Allan Kay

(57) ABSTRACT

A new and distinct cultivar of *Anthurium* plant named 'KARINA' is disclosed, characterized by a small, compact size, and red spathes with distinct veins. Spathe production is abundant. Spathes are broad and ovate. Plants are fast-growing, flowering within 9 months from emerging of tissue culture. The new cultivar is an *Anthurium,* typically produced as an ornamental plant.

2 Drawing Sheets

Figure 1:
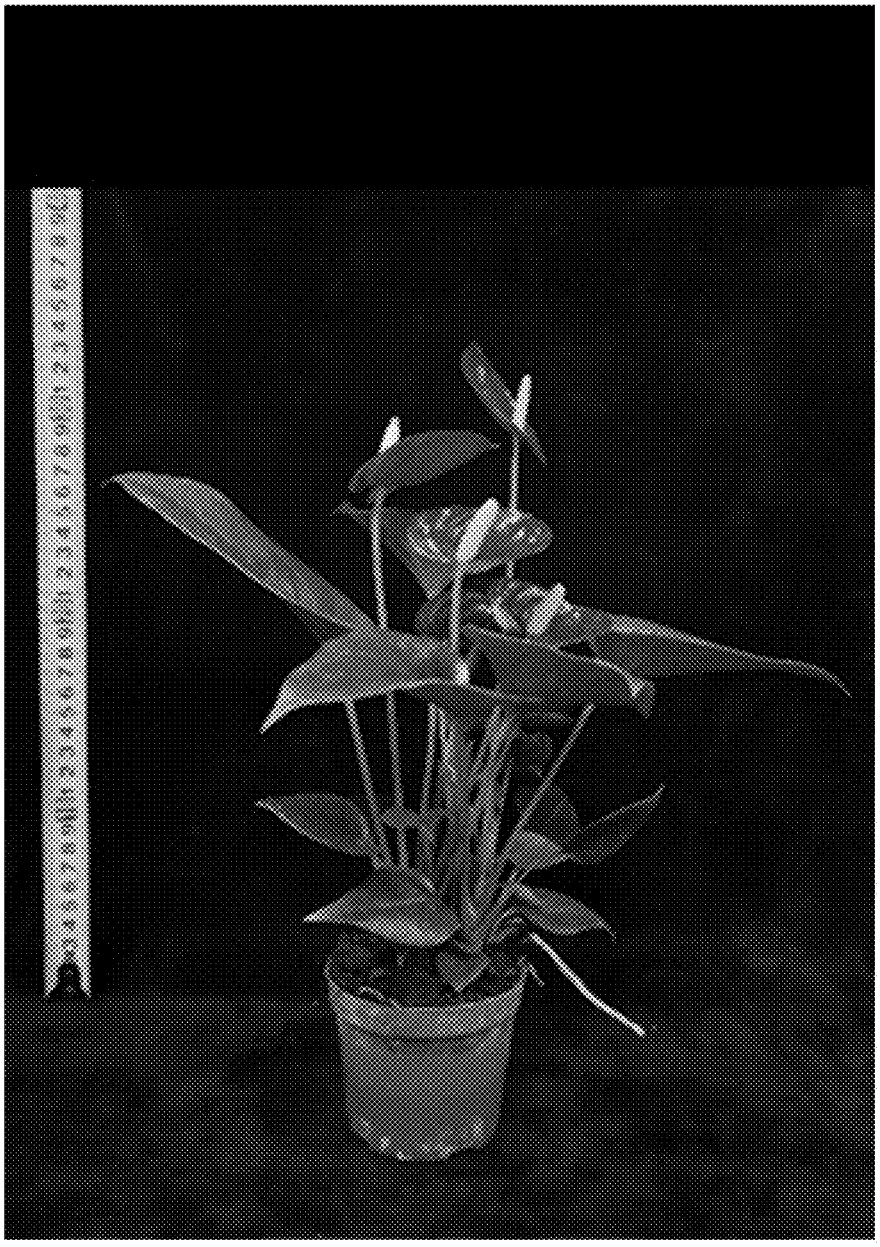

Latin name of the genus and species: *Anthurium andraeanum.*

Cultivar denomination: 'KARINA'.

BACKGROUND OF THE INVENTION

The new cultivar is a product of a planned breeding program by the inventor. The new cultivar originated from a crossing of the seed parent, the unpatented *Anthurium* 'Red Success', and the pollen parent, *Anthurium* 'Orange Champion', unpatented. The crossing was made at a greenhouse facility in Zhongshan, Guangdong, China in March 2016.

The new cultivar was discovered by the inventor in 2017 in a group of seedlings resulting from the crossing, at the same location in Zhongshan, Guangdong, China.

Asexual reproduction of the new cultivar 'KARINA' was first performed by tissue culture in a commercial tissue culture laboratory in Zhongshan, Guangdong, China in June 2017. Subsequent propagation has shown that the unique features of this cultivar are stable and reproduced true to type.

SUMMARY OF THE INVENTION

The cultivar 'KARINA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KARINA.' These characteristics in combination distinguish 'KARINA' as a new and distinct *Anthurium* cultivar:

1. Small and compact plant type.

2. Fast growth rate; 9 months from the emergence of tissue-culture to flowering.
3. Abundant flowers with red spathes.
4. The spathe has distinct veins and a strong vesicular texture; when the anthers are about to dehisce, the apex of the spadix is yellow while the base is white.
5. Leaves are medium-sized and ovate; spathes are broad and ovate.

PARENT COMPARISONS

'KARINA' can be compared to the seed parent in most horticultural characteristics, however, 'KARINA' differs in the following:

1. Plants of the new cultivar are compact, while plants of the seed parent are relatively loose.
2. Young leaf color of the new cultivar is yellow-green, while the young leaf color of the seed parent is green.
3. Spathes of the new cultivar grow higher than the leaves, while the spathes of the seed parent are the same height as the leaves.

'KARINA' can be compared to the pollen parent in most horticultural characteristics, however, 'KARINA' differs in the following:

1. Plants of the new cultivar are small and compact, while plants of the pollen parent are large and upright.
2. Young leaf color of the new cultivar is a darker yellow-green than the young leaf color of the pollen parent.
3. Mature leaf color of the new cultivar is a more neutral green, while the young leaf color of the pollen parent is a brighter green.

4. Spathe color of the new cultivar is red, while the spathe color of the pollen parent is orange.

COMMERCIAL COMPARISONS

'KARINA' can be compared to the commercial cultivar *Anthurium* 'Joli', unpatented. Plants of 'Joli' are similar to plants of 'KARINA' in most horticultural characteristics, however, 'KARINA' differs in the following:

1. Mature leaf color of the new cultivar is a more neutral green, while the young leaf color of this comparator is a brighter green.
2. Spathe color of the new cultivar is red, while the spathe color of this comparator is pink-purple.
3. When the spadix of the new cultivar is about to dehisce, its tip is yellow and its base is white; when the spadix of this comparator is about to dehisce, it is pink-purple.

'KARINA' can be compared to the commercial cultivar *Anthurium* 'Royal Pink Champion', unpatented. Plants of 'Royal Pink Champion' are similar to plants of 'KARINA' in most horticultural characteristics, however, 'KARINA' differs in the following:

1. Mature leaf color of the new cultivar is a more neutral green, while the young leaf color of this comparator is a brighter green.
2. Spathe color of the new cultivar is red, while the spathe color of this comparator is pink.
3. When the spadix of the new cultivar is about to dehisce, its tip is yellow and its base is white; when the spadix of this comparator is about to dehisce, it is pink-purple.
4. Plants of the new cultivar are small, while plants of this comparator are medium-size.

BRIEF DESCRIPTION OF THE PHOTOGRAPHS

The accompanying photograph in FIG. 1 illustrates in full color a typical plant of 'KARINA' grown in a greenhouse in Zhongshan, Guangdong, China. This plant is approximately 12 months old, shown in an 8 cm pot.

Figure 2:
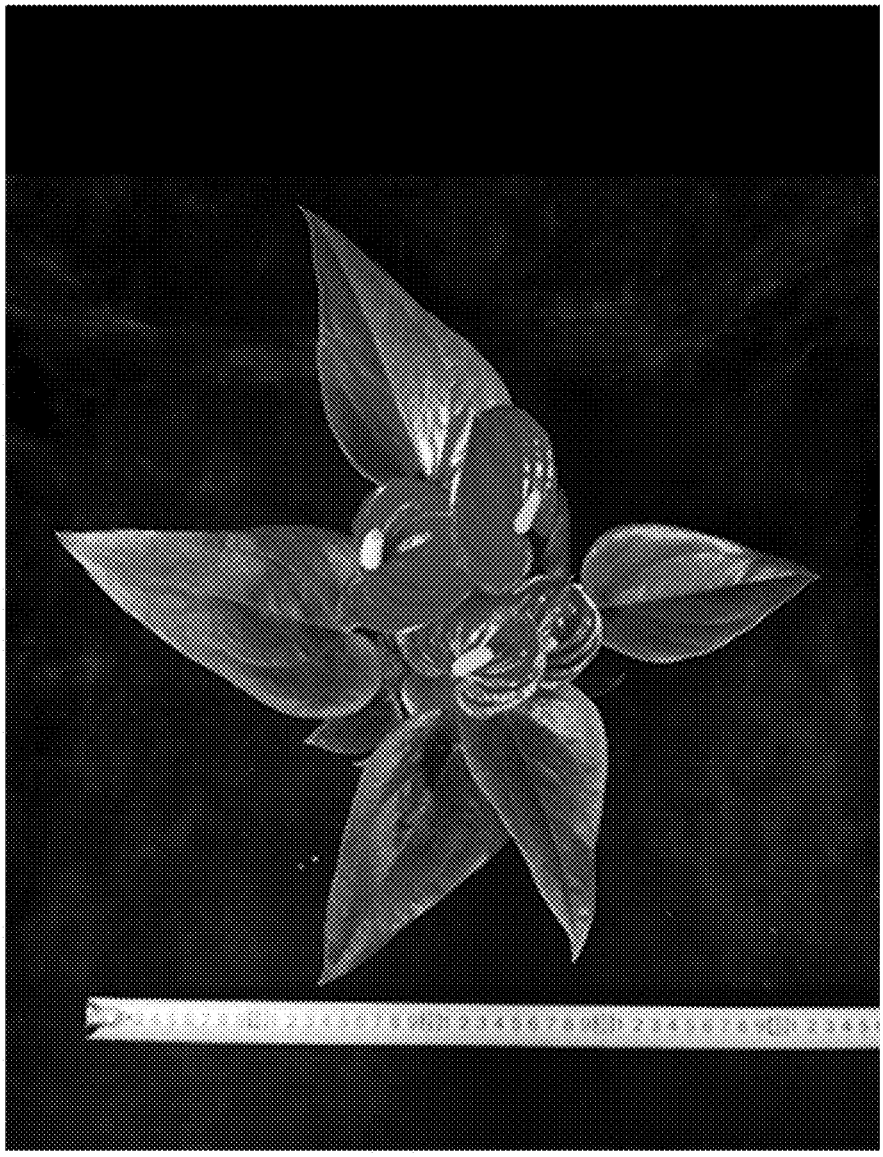

FIG. 2 is a top-down view of the same plant as FIG. 1.

The photographs were taken using conventional techniques and although colors may appear different from actual colors due to light reflectance they are as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KARINA' plants grown in a greenhouse in Fujian, China during the summer. Temperatures ranged from 18° C. to 23° C. at night to 20° C. to 28° C. during the day. No artificial light, photoperiodic treatments were given to the plants. Measurements and numerical values represent averages of typical plant types.

Botanical classification: *Anthurium andraeanum* 'KARINA'.

PROPAGATION

Time to initiate roots: Approximately 15 days at approximately 25° C.

Time to produce a fully rooted plantlet: Approximately 4 weeks at approximately 25° C.

Root description: Adventitious roots, fleshy, light yellow.

PLANT

Growth habit: Compact clumping habit, no trailing stems.

Plant shape: Rosette-shaped with a compact outline.

Height: Approximately 21 cm to top of highest leaf; approximately 27 cm to top of highest inflorescence.

Plant spread: Approximately 33 cm.

Container size: 8 to 13 cm.

Growth rate: Fast.

Branching characteristics: No branching. Leaves emerge directly from base of plant.

Number of clumps: 1.

Number of leaves per clump: Approximately 6.

Number of leaves per plant: Approximately 6.

FOLIAGE

Leaf:

*Arrangement*.—Rosulate.

*Average length*.—Approximately 13.5 cm.

*Average width*.—Approximately 7.9 cm.

*Shape of blade*.—Ovate.

*Aspect*.—Upward-curving.

*Apex*.—Acuminate.

*Base*.—Cordate.

*Margin*.—Entire.

*Texture of top surface*.—Stiff and leathery.

*Texture of bottom surface*.—Glabrous and shiny.

*Color*.—Young foliage, upper side: Near RHS Yellow-Green 146A. Young foliage, under side: Near RHS Yellow-Green 148A. Mature foliage, upper side: Near RHS Green NN137A. Mature foliage, under side: Near RHS Yellow-Green 146B.

Venation:

*Type*.—Pinnate.

*Color*.—Upper side: Near RHS Green NN137B. Under side: Near RHS Yellow-Green 146C.

Petiole (excluding geniculum):

*Length*.—Approximately 11 cm.

*Width*.—At geniculum: Approximately 0.34 cm. Above clump: Approximately 0.30 cm.

*Color*.—Near RHS Yellow-Green 146A.

*Strength*.—Moderate to strong.

INFLORESCENCE

Arrangement: Solitary, arising from the base of leaves.

Flowering habit: Continuous flowering under suitable conditions.

Quantity of spathes per plant: On average 3 fully open spathes in good condition.

Natural flowering season: Year-round under suitable growing conditions.

Time to flowering: Approximately 9 months from the emergence of tissue-cultured seedlings.

Fragrance: None.

Self-cleaning or persistent: Persistent.

Flower longevity: Flowers stay in good condition approximately 4-6 weeks on the plant.

Spathe:

*Aspect*.—Upward-curving.

*Length*.—Approximately 5 cm.

*Width*.—Approximately 6 cm.
*Shape*.—Broadly ovate.
*Margin*.—Entire.
*Apex*.—Acute.
*Base*.—Cordate.
*Color*.—Front when opening: Near RHS Red N45A. Back when opening: Near RHS Red N45B. Front when mature: Near RHS Red N45A. Back when mature: Near RHS Red 46B. Fading to: Near RHS Green NN137A, with the entire spathe gradually transitioning to green as it senesces.

Spadix:
*Shape*.—Cylindrical.
*Tip*.—Rounded.
*Base*.—Attenuate.
*Length*.—Approximately 2.8 cm.
*Width*.—Approximately 0.66 cm.
*Color*.—When opening: Near RHS Yellow-White 158D. Mature: Near RHS Yellow 162A.
*Quantity of flowers per spadix*.—Approximately 120-150.
*Spadix flower arrangement*.—Dense, spirally arranged.
*Spadix flower diameter*.—Approximately 0.12 cm.
*Spadix flower depth*.—Approximately 0.22.

Peduncle:
*Length*.—Approximately 17.5 cm.
*Width*.—Approximately 3.1 cm.
*Color*.—Near RHS Yellow-Green 146B.
*Strength*.—Moderate.

REPRODUCTIVE ORGANS

Not clearly visible.

SEEDS

*Shape*.—Oval.
*Length*.—Approximately 0.2-0.3 mm.

Seeds mature approximately 4-6 months after successful pollination.

OTHER CHARACTERISTICS

Disease resistance: No resistance or susceptibility to typical diseases and pests of *Anthurium* have been observed.
Drought tolerance and temperature tolerance: No distinctive resistance beyond common varieties of *Anthurium* have been observed.
Fruit production: Not observed.

What is claimed is:

1. A new and distinct cultivar of *Anthurium* plant named 'Karina' as herein illustrated and described.

* * * * *